United States Patent
Tamhankar et al.

[11] Patent Number: 6,002,019
[45] Date of Patent: Dec. 14, 1999

[54] PROCESS FOR THE PRODUCTION OF PETROCHEMICALS

[75] Inventors: Satish S. Tamhankar, Scotch Plains; Divyanshu R. Acharya, Bridgewater; Sidney Simon Stern, Highland Park, all of N.J.

[73] Assignee: The Boc Group, Inc., Murray Hill, N.J.

[21] Appl. No.: 08/975,269

[22] Filed: Nov. 21, 1997

Related U.S. Application Data

[63] Continuation of application No. 08/457,003, Jun. 1, 1995, abandoned.

[51] Int. Cl.[6] ...................... C07C 253/24; C07C 253/26; C07D 307/34
[52] U.S. Cl. ........................... 549/258; 95/143; 422/171; 422/190; 549/259; 549/523; 558/319; 558/320; 568/476; 570/224; 585/820; 585/826
[58] Field of Search ..................... 585/747, 800, 585/820, 826; 549/249, 258, 259, 523; 423/210; 208/99; 95/143, 148; 422/171, 190; 558/319, 320; 568/476; 570/224

[56] References Cited

U.S. PATENT DOCUMENTS

| | | |
|---|---|---|
| 3,069,362 | 12/1962 | Mays et al. . |
| 3,069,363 | 12/1962 | Mays et al. . |
| 3,649,559 | 3/1972 | Cooper ........................ 95/143 |
| 3,732,326 | 5/1973 | Chen ........................... 95/143 |
| 4,987,239 | 1/1991 | Ramachandran et al. .......... 549/250 |
| 5,126,463 | 6/1992 | Rmachandran et al. ........... 549/262 |
| 5,262,547 | 11/1993 | Ramachandran et al. .......... 549/262 |
| 5,278,319 | 1/1994 | Ramachandran et al. .......... 549/249 |
| 5,458,675 | 10/1995 | Morlec et al. ................. 95/143 |

FOREIGN PATENT DOCUMENTS

| | | | |
|---|---|---|---|
| 297076 | 1/1992 | Germany ........... 95/143 |
| 62-289217 | 12/1987 | Japan ............... 95/143 |

OTHER PUBLICATIONS

International Publication No. WO 84/04913, Dec. 20, 1984.

*Primary Examiner*—Wayne Langel
*Attorney, Agent, or Firm*—Coleman R. Reap; Salvatore P. Pace

[57] ABSTRACT

Petrochemicals are produced by the vapor phase reaction of a hydrocarbon with air in the presence of a suitable catalyst. The petrochemical product is removed from the product gas stream, and part or all of the remaining gas stream is passed through a bed of hydrophobic adsorbent, which adsorbs mainly the unreacted hydrocarbon from the gas stream without adsorbing water vapor. The adsorbed hydrocarbon is purged from the bed with air, and the air-hydrocarbon mixture is recycled to the partial oxidation reactor.

32 Claims, 1 Drawing Sheet

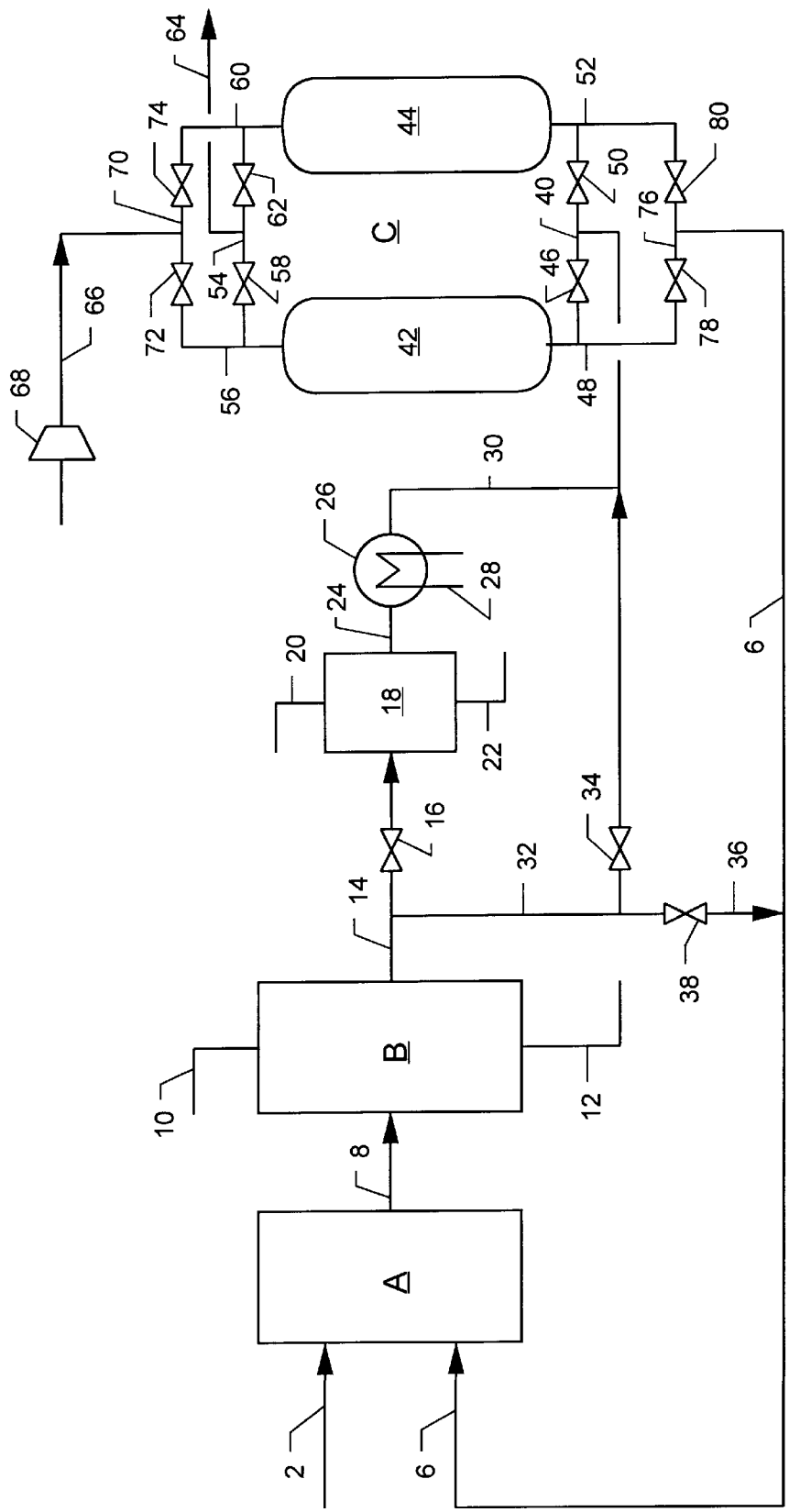

PROCESS FOR THE PRODUCTION OF PETROCHEMICALS

This is a continuation of Application Ser. No. 08/457,003, filed Jun. 1, 1995, abondoned.

FIELD OF THE INVENTION

The present invention is directed to a process for producing petrochemicals from a hydrocarbon and an oxygen-containing gas in the presence of a suitable catalyst, and more particularly to a hydrocarbon partial oxidation process in which unreacted hydrocarbon separated from other components of a gaseous waste stream is recycled to the partial oxidation reactor.

BACKGROUND OF THE INVENTION

Certain petrochemicals are produced commercially by the partial oxidation of an appropriate hydrocarbon in the vapor phase over a suitable catalyst and in the presence of an oxygen-containing gas. For example, cyclic anhydrides are produced commercially by the vapor phase catalytic partial oxidation of aromatic hydrocarbons, such as o-xylene or benzene, or straight-chain hydrocarbons, such as n-butane, or butene, in the presence of an oxygen-containing gas, over a vanadium-containing catalyst. Similarly, nitrites, alkylene oxides, aldehydes and halogenated hydrocarbons are produced by the partial oxidation of appropriate alkanes and alkenes in the presence of selected catalysts. Air is generally used as the oxygen-containing gas, because of its low cost and ready availability. Oxygen-enriched air is also used. The reaction can be carried out in any suitable reactor, such as a fixed bed, a fluidized bed, a moving bed, a trickle bed or a transport bed reactor, and it produces the petrochemical, and generally carbon monoxide (CO), carbon dioxide ($CO_2$), water, and smaller amounts of other partially oxidized by-products. The reaction equipment train generally consists of a reactor, in which the petrochemical product is produced, a scrubber, in which the petrochemical product is scrubbed from the reactor effluent gases by means of water or other solvent for the petrochemical, and means for further treating the scrubbed effluent gases.

Currently, it is common to practice the above-described process on a single pass basis with the conversion of hydrocarbon to the desired petrochemical product being maximized. This results in a low overall efficiency, since the selectivity to petrochemical product is below the maximum. Consequently, the scrubber effluent gas contains considerable amounts of CO and $CO_2$, in addition to unreacted hydrocarbon. These products are usually incinerated, so that the only return realized from them is heat value. In modified processes, a portion of the scrubber effluent gas is recycled, the conversion of the hydrocarbon feedstock is lowered and the selectivity of hydrocarbon conversion to the desired petrochemical product is increased. The remainder of the effluent are purged from the system to prevent the build-up of CO, $CO_2$ and nitrogen (introduced into the system when air is used as the source of oxygen). These improvements results in a reduced "per pass" conversion, but the overall efficiency of the process is increased.

Federal Republic of Germany (FRG) Patent Application Disclosure 25 44 972 discloses a maleic anhydride manufacturing process in which the reactor feed comprises $C_4$ hydrocarbons, air, CO and $CO_2$. In the process of this patent, maleic anhydride is recovered from the reactor effluent gas stream and a portion of the remaining stream is recycled to the reactor. This patent also teaches recovering butane by temperature swing adsorption (TSA) from the non-recycled gas stream and recycling the recovered butane to the reactor. The butane is desorbed from the adsorbent at elevated temperature using fresh air as the purge gas, and the air-butane mixture is recycled to the reactor.

U.S. Pat. No. 4,231,943 discloses the production of maleic anhydride by the reaction of n-butane and air in the presence of a catalyst comprising vanadium and phosphorus oxides. The process of this patent includes the steps of recovering maleic anhydride from the gaseous oxidation reactor effluent, directly recycling a portion of the maleic anhydride-free effluent to the reactor, separating relatively pure n-butane from the remaining gaseous effluent and recycling the relatively pure n-butane to the feed stream.

U.S. Pat. No. 4,987,239 discloses a process for the production of anhydrides by the partial oxidation reaction of a hydrocarbon with an oxygen-containing gas in the presence of a suitable catalyst. In the process of this patent, the gaseous effluent from the maleic anhydride product scrubber is compressed and sent to a selective separator, e.g. a pressure swing adsorption (PSA) unit, wherein a substantial proportion of the unreacted hydrocarbon contained in the effluent is recovered, and the unreacted hydrocarbon and a controlled amount of a gaseous flame suppressor is recycled to the partial oxidation reactor.

The above patents do not discuss or make allowance for moisture contained in the gaseous effluent from the partial oxidation product recovery unit and in purge air, when ambient air is used to purge the adsorbent that is employed to separate hydrocarbons from the waste gas stream. Moisture is produced in the partial oxidation reaction; accordingly, the hot gaseous effluent from the reactor contains moisture. As the effluent gas passes through the product scrubber some moisture may be removed by condensation due to cooling of the gas stream, if an aqueous solvent is used. When a nonaqueous solvent is used moisture is not permitted to condense. In any event, the gas stream leaving the scrubber still contains moisture, and in fact can be saturated with moisture, even if a nonaqueous scrubbing agent is used. Moisture is more strongly adsorbed than the unreacted hydrocarbons and carbon oxides by conventional adsorbents; accordingly, unless the moisture is removed from the gas stream entering the adsorption units, it will be preferentially adsorbed onto the adsorbent, thereby reducing the capacity of the adsorbent for hydrocarbon adsorption.

The problem of moisture is further aggravated when ambient air is used as a purge gas for regeneration of the beds of adsorbent. Ambient air contains moisture; thus, moisture will replace the hydrocarbon being desorbed from the adsorption beds during the purge step when the beds are purged with the air. This will further reduce the capacity of the adsorbent during the adsorption step of the following cycle.

It is known to remove moisture from ambient air or a gas stream by various techniques. For example the air and gas streams can be dried by passing the air and gas stream through desiccants.

Because of their industrial importance, recycle partial oxidation processes in which problems such as those noted above are eliminated or minimized are constantly sought. The present invention provides a recycle partial oxidation process which avoids the necessity of employing complex and costly drying equipment arrangements.

SUMMARY OF THE INVENTION

The present invention is an improvement in a recycle process for manufacturing a petrochemical by the partial oxidation of a hydrocarbon using air in the presence of a swuiable catalyst under reduced conversion conditions. The reactor effluent contains the petrochemical asmthe rain product, water as a by-product, and unreacted hydrocarbon. The petrochemical is removed from the reactor effluent in a petrochemical recovery unit, and hydrocarbon is adsorbed from the petrochemical unit waste gas using one of certain hydrophobic adsorbents. The invention includes as steps, purging adsorbed hydrocarbon from the adsorbent with ambient air and recycling the purged hydrocarbon-air mixture to the partial oxidation reactor.

A first embodiment of the invention comprises the steps:

(a) contacting in a reaction zone a hydrocarbon with an oxygen-containing gas selected from air and oxygen-enriched air in the presence of an appropriate oxidation catalyst under conditions which produce a product gas comprising, inter alia, the petrochemical, unreacted hydrocarbon, and moisture;

(b) removing the petrochemical from the product gas in a petrochemical recovery zone;

(c) passing at least part of the petrochemical-free gas remaining after step (b) through a hydrocarbon-selective hydrophobic adsorbent, thereby adsorbing unreacted hydrocarbon onto the adsorbent and producing hydrocarbon-depleted waste gas;

(d) at least partially regenerating the hydrophobic adsorbent by passing said oxygen-containing gas therethrough, thereby producing a gaseous stream comprising desorbed hydrocarbon and oxygen-containing gas; and (f) recycling at least part of the gaseous stream comprising desorbed hydrocarbon and air to the reaction zone.

In one embodiment, all of the petrochemical-free gas stream is passed through the hydrophobic adsorbent. In another, part of this gas stream is passed through the adsorbent, and the rest is recycled directly to the reaction zone.

In general, the hydrophobic adsorbent is a metal cation-free molecular sieve having a silicon-to-aluminum atomic ratio greater than about 100:1, and is selected from type Y zeolite, type ZSM-5 zeolite, type ZSM-11 zeolite, type ZSM-20 zeolite, silicalite-1, silicalite-2, and mixtures of these. In a preferred embodiment, the adsorbent is selected from type Y zeolite, type ZSM-5 zeolite, silicalite-1 and mixtures of these, and in the most preferred embodiment, the adsorbent is silicalite.

In a preferred embodiment steps (c) and (d) are steps of a cyclic adsorption process selected from concentration swing adsorption (CSA) and PSA. In a more preferred embodiment, steps (c) and (d) are carried out at the same or different pressures, and these pressures are in the range of about 1.2 to about 5 bara. In one preferred aspect, steps (c) and (d) are carried out at substantially the same pressure, i.e. the process is CSA, and in a more preferred aspect, this pressure is in the range of about 1.2 to about 1.75 bara. In another preferred aspect, steps (c) and (d) are carried out at different pressures, i.e. the process is PSA, and in a more preferred aspect, step (c) is carried out at a pressure in the range of about 1.2 to about 1.75 and step (d) is carried out at a pressure in the range of about 1 to about 1.5 bara. In a variant of the latter preferred aspect, between steps (c) and (d) there are the additional steps of desorbing hydrocarbon from said hydrocarbon-selective adsorbent by depressurization and recycling said desorbed hydrocarbon to said reaction zone.

In another preferred embodiment of the invention, the relative humidity of one or both the petrochemical-free gas stream and the oxygen-containing gas are reduced prior to passing these gases through the bed of hydrophobic adsorbent. In one aspect of this embodiment, the relative humidity of the petrochemical-free gas stream is reduced by heating this stream. In a further modification, the petrochemical-free gas stream is passed through a direct contact water cooler prior to heating this stream. This stream can be heated by compression or by means of a heater. In another aspect of this embodiment, the relative humidity of said oxygen-containing gas is reduced by heating it prior to step (d). This stream can also be heated by compression. As an alternative to heating the petrochemical-free gas, the hydrophobic adsorbent can be heated to a temperature that is higher than the temperature of the petrochemical-free gas.

In other preferred embodiments, the oxygen-containing gas is air; the hydrophobic adsorbent is silicalite; the cyclic anhydride is maleic anhydride and the hydrocarbon is n-butane.

BRIEF DESCRIPTION OF THE DRAWING

The FIGURE illustrates, in a block diagram, a system in which preferred embodiments of the process of the invention can be carried out.

DETAILED DESCRIPTION OF THE INVENTION

The improvement of the invention can be applied to any partial oxidation reaction in which a gaseous hydrocarbon is reacted with oxygen, provided in the form of air, in the presence of an appropriate catalyst to produce a gaseous product stream containing the petrochemical, unreacted hydrocarbon and moisture; the petrochemical is separated from the gaseous product stream; unreacted hydrocarbon is adsorbed from the remaining gaseous product stream by adsorption; and the separated hydrocarbon is desorbed from the bed of adsorbent and recycled to the partial oxidation reactor. Typical of such processes are those used to manufacture cyclic anhydrides, such as maleic anhydride, alkylene oxides, such as ethylene oxide, aldehydes, such as acetaldehyde, nitrites, such as acrylonitrile, and chlorinated hydrocarbons, such as vinyl chloride. The details of such partial oxidation reaction-based processes are well known and form no part of the present invention. These processes are described in detail in U.S. Pat. Nos. 5,126,463, 5,262, 547, and 5,278,319, the specifications of which are incorporated herein by reference.

The petrochemical manufacturing processes in which the subject invention is employed are those in which some or all of the oxygen-containing gas that is used in the partial oxidation reaction is introduced into the system in the hydrocarbon recovery section of the plant as a purge gas to purge adsorbed hydrocarbon from the adsorbent. The oxygen-containing gas may be atmospheric air, i.e. air obtained directly from the atmosphere, or oxygen-enriched atmospheric air. By oxygen-enriched air is meant air that contains more oxygen than is naturally present in air. Oxygen-enriched air may be prepared by introducing oxygen into air or by removing nitrogen from the air. Air is preferred since it is inexpensive and readily available. Supplemental oxygen-containing gas may be supplied directly to the reactor, if desired. For ease of description, the oxygen-containing gas used in the process of the invention will be generally referred to in the following discussion as air.

The adsorbents used in the process of the invention are substantially metal cation-free and alumina-deficient, i.e.

their lattice structures are substantially free of alumina groups. Specifically, they have silicon to aluminum atomic ratios of at least 100. As this ratio increases the hydrophobicity of the adsorbent improves. Included in this group of adsorbents are molecular sieves of the FAU, MFI and MEL type structures, including zeolites that have been made alumina-deficient by dealumination and molecular sieves that are directly synthesized without introducing alumina groups into the lattice structure. Alumina-deficient molecular sieves useful in the invention include dealuminated type Y zeolite (DAY), ZSM-5, ZSM-11 and ZSM-20, all having silicon to aluminum atomic ratios of at least about 100. Other synthesized molecular sieves that are substantially free of alumina groups which are useful in the invention include those having structures analogous to ZSM-5 and ZSM-11, known as silicalite-1 and silicalite-2, respectively each of which are substantially free of alumina groups in their structures. Preferred molecular sieves are DAY, alumina-deficient ZSM-5 and silicalite-1, all of which are substantially metal cation-free and all of which are commercially available. For purposes of this invention the term "metal cation-free" means that the adsorbent contains no more than trace amounts of metal cations, and the terms "alumina-deficient" and "dealuminated", when used in reference to molecular sieves mean that the ratio of silicon to aluminum atoms in the sieves is at least about 100:1, i.e., the ratio of silica to alumina groups in the sieve is at least 200:1. Suitable adsorbents are commercially available and their preparation forms no part of the invention.

The invention can be better understood from the accompanying drawing. Depicted in the drawing as essential equipment units, are hydrocarbon partial oxidation reactor A, petrochemical product recovery unit B and separator C. Auxiliary equipment, including valves, compressors and heat exchangers, which are unnecessary for an understanding of the invention have been omitted from the drawing to simplify discussion of the invention.

On its inlet end, reactor A is provided with hydrocarbon feed inlet means 2 and hydrocarbon recycle and air supply line 6. On its outlet end reactor A is provided with product gas discharge line 8. Reactor A may be any suitable reactor, such as, for example, those of the fixed, moving, fluidized, or transport catalyst bed design. Reactor A may be equipped with heat exchange means (not shown) to remove heat developed in the reaction, which is exothermic. The design details of partial oxidation reactors are well known and they form no part of the present invention.

Line 8 is connected to the petrochemical feed inlet of petrochemical product recovery unit B, which may be any unit that functions to separate petrochemical partial oxidation products from byproduct gases. For example, unit B may be a conventional gas scrubber, i.e. an absorber, of, for example, the packed bed design, or it may be a condenser or other appropriate product recovery unit. It is here illustrated as equipped with means for spraying water or an aqueous or nonaqueous liquid on the product gas entering this unit from reactor A. To simplify the description of the process of the invention, recovery unit B will be referred to as a scrubber. Scrubber B receives a scrubbing liquid through inlet 10 and discharges a liquid product through outlet 12. Scrubber B is also equipped with a scrubbed gas outlet 14 which, in the embodiment illustrated in the drawing, communicates through valve 16 with the inlet of cooler 18.

Cooler 18 may be any gas cooling means, such as a direct contact cooler. Cooler 18 is provided with cool water supply line 20 and cool water return line 22. On its gas outlet end, cooler 18 is provided with cooled gas outlet line 24, which communicates with the inlet of heater 26. Heater 26 may be any heating means, and it is depicted in the drawing as a heat exchanger. A hot medium circulating through heating coil 28 serves to heat the gas passing through heater 26. On its outlet end heater 26 is provided with heated gas transfer line 30.

In some cases cooler 18 and/or heater 26 are not necessary. In such cases these units may be bypassed or eliminated. Heater bypass line 32, fitted with valve 34, provides fluid communication between line 14 and heated gas transfer line 30. Direct petrochemical-free gas recycle line 36, fitted with valve 38 joins line 14 to hydrocarbon recycle line 6. Gas transfer line 30 is connected to separator C inlet manifold 40.

Separator C may comprise a single adsorption unit or battery of adsorption units operated in phase, or a plurality of adsorption units or batteries of adsorption units operated out of phase, whichever is desired. When a system comprising a single adsorption unit or an "in phase" battery of units is used, the adsorption step must be periodically stopped to permit regeneration of the adsorbent bed(s), whereas when a plurality of adsorption units are employed in parallel and operated out of phase, one or more units can be in adsorption service producing purified adsorbate, while one or more other units are undergoing regeneration to release the adsorbed hydrocarbon. Operation of the hydrocarbon adsorption system is cyclical. A partial cycle (half-cycle) occurs when one bed has undergone all of the steps in the adsorption process, and a full cycle occurs when each bed of the adsorption system has undergone a partial adsorption cycle. In the complete adsorption process full cycles are repeatedly carried out, so that the process is substantially continuous. In the preferred embodiment of the invention, separator C is a twin bed system comprising a pair of parallel vessels, 42, 44, each packed with one or more hydrophobic adsorbents of the type described above and operated 180° out of phase, and the invention will be described in detail as practiced in such an arrangement. It is understood, however, that the illustrated system is merely exemplary of systems suitable for practicing the process of the invention.

Feed gas entering feed manifold 40 can be directed to vessel 42 via valve 46 and line 48 or to vessel 44 through valve 50 and line 52. On the outlet end of separator C, nonadsorbed gas passes out of vessel 42 and into nonadsorbed gas outlet manifold 54 through line 56 and valve 58 and out of vessel 44 through line 60 and valve 62. Nonadsorbed gas outlet manifold communicates with nonadsorbed gas discharge line 64. Separator C is also provided on its nonadsorbed gas outlet end with purge air supply line 66, which is provided with air pump device 68. Line 66 is connected to purge gas manifold 70, which communicates with line 56 through valve 72 and line 60 through valve 74. On the inlet end of separator C, lines 48 and 52 communicate with purged gas manifold 76 through valves 78 and 80, respectively. Manifold 76 communicates with hydrocarbon recycle line 6.

In carrying out the process of the invention, a gaseous hydrocarbon and the oxygen-containing gas are introduced into reactor A via feed lines 2 and 6 respectively. The feed gases entering reactor A contact the catalyst contained therein and react to form the desired petrochemical product. The product gas stream leaving reactor A contains, in addition to the desired petrochemical, carbon dioxide, carbon monoxide and water as by-products. The product stream generally also contains unreacted hydrocarbon, oxygen and nitrogen, and may contain small amounts of other by-products, impurity gases and nonreactive hydrocarbons, as well. In the embodiment illustrated in the drawing, the product gas stream leaves reactor A via line 8 and enters petrochemical product scrubber B. The purpose of unit B is to remove the petrochemical product from the hydrocarbon reactor effluent gas. In scrubber B the product gases are intimately contacted with a solvent for the petrochemical product, which enters scrubber B through line 10. The solvent, which may be water or an aqueous liquid, or a nonaqueous solvent, dissolves substantially all of the petrochemical product out of the product gas stream. The petrochemical product-containing solution leaves scrubber B via line 12 and is usually further treated to recover the petrochemical product.

The scrubbed gas stream leaves scrubber B through line 14, and part or all of this stream is next treated to recover unreacted hydrocarbon from the stream. This is accomplished by passing the scrubbed gas through separator C, which contains a hydrophobic adsorbent that adsorbs hydrocarbons in preference to the other gaseous components in the scrubbed gas. The use in separator C of the particular hydrophobic adsorbents described above provides two important benefits. Firstly, it makes possible the efficient removal of hydrocarbons from the moisture-laden scrubbed gas stream without first removing moisture from this stream. If separator C were packed with a conventional adsorbent, it would be necessary to remove water from the scrubbed gas stream prior to passing it into separator C; otherwise the capacity of the adsorbent would be severely reduced by the preferential adsorption of water vapor.

The second advantage of using the selected hydrophobic adsorbents in separator C is that this permits purging of adsorbed hydrocarbon from the adsorbent using ambient air (which contains moisture) as a purge gas without loading the adsorbent with water. If conventional adsorbents were used, it would usually be necessary to remove water vapor from the air prior to its introduction into separator C. The moist air leaving the adsorption units in the purge gas stream can be used to provide part or all of the oxygen requirement for the partial oxidation reaction, since the use of moist air as a source of oxygen is not detrimental to the partial oxidation reaction taking place in reactor A.

As can be seen in the drawing, the scrubbed gas effluent from unit B can be further processed in a variety of ways, the particular treatment selected depending uponr inter alia, the particular adsorbent used in separator C, and the volume of byproduct gases in the scrubber B effluent.

As one option, the relative humidity of part or all of the scrubbed gas can be reduced, i.e. the scrubbed gas can be desaturated. This is preferable when the scrubbed gas is fully saturated with moisture, i.e. when its relative humidity is 100%. Although some,hydrophobic adsorbents can function with fully moisture-saturated gases without suffering adverse effects, it is usually preferred that the gas be somewhat less than 100% saturated with moisture. This reduces the risk of condensation of moisture onto the adsorbent, which would damage the adsorbent. It is often desirable to reduce the relative humidity of the scrubbed gas to about 90% or lower, and most preferred to reduce it to about 80% or lower.

Reduction of the relative humidity of the scrubbed gas can be accomplished in a number of ways. It can be cooled sufficiently to cause some of the moisture in the stream to condense, and then heated, thus causing the relative humidity to drop. This option is illustrated in the embodiment shown in the drawing. In practicing this embodiment, valve 16 is opened and part or all of the gas passing through line 14 flows into direct contact cooler 18. In cooler 18, the gas is sprayed with cool water, which enters cooler 18 through line 20 and leaves through line 22. This technique also serves to scrub solid impurities and trace chemicals, such as acids, from the gas stream. As the cool water contacts the gas it causes it to become supersaturated with moisture. The excess moisture condenses out of the gas. The cooled water-saturated gas then passes through line 24 and into heat exchanger 26, wherein it is heated by indirect contact with the heating medium passing through coil 28 of the heater. As the temperature of the gas rises, its relative humidity drops.

In some cases, it may be preferable t6 simply heat the gas without first cooling it to the point of supersaturation. Heating the gas increases its moisture capacity, thereby reducing its relative humidity. In such cases, cooler 18 is not necessary and can be eliminated from the system.

Heating of the gas stream can be accomplished by means other than the heat exchange embodiment shown in the drawing. For example, the gas can be heated by compressing it. This procedure is convenient when it is desired to raise the pressure of the gas stream prior to introducing it into separator C.

The relative humidity of the gas stream leaving scrubber B can also reduced by desaturating only part of this stream, i.e. by causing some of the gas from scrubber B to pass through cooler 18 and sending the remainder of this stream directly to separator C, by opening valve 34. This variation permits the use of smaller heating and/or cooling equipment. The desaturated gas stream is recombined with the bypass stream. This will generally reduce the moisture content of the combined stream to the desired extent.

In some cases, it may not be considered necessary or desirable to reduce the relative humidity of any of the scrubbed gas prior to its introduction into separator C. This is the case when the relative humidity of the gas stream is already less than 100%, or when a hydrophobic adsorbent that functions efficiently at 100% relative humidity is used. In these cases all of the scrubbed gas going to scrubber C goes there directly from scrubber B. This is accomplished by opening valve 34 and maintaining valve 16 in the closed position.

In each of the above cases, it is only necessary to remove in each pass through the system sufficient byproduct gases (carbon oxides and moisture) and inert gases (nitrogen and argon) to prevent the buildup of these gases in the system. This is accomplished when the quantity of carbon oxides and moisture removed from the system is equivalent to the amount of byproduct generated in reactor B, and when the quantity of inert gases removed is equivalent to the quantity of inert gases introduced into the system in each pass. Thus, it is usually desirable to send to separator C only the volume of scrubbed gas that is necessary to maintain the proper material balance. The remainder of the scrubbed gas stream can be recycled directly to reactor A. This is done by opening valve 38.

The process of the invention is generally practiced as a cyclical process, such as PSA, VSA (vacuum swing adsorption—a variation of PSA wherein the adsorption step is carried out at low pressures and the regeneration step is conducted under vacuum), CSA (concentration swing adsorption—a cyclical adsorption process conducted at any desired temperature and pressure in which a gas is first adsorbed onto an adsorbent, and the adsorbent is regenerated by flushing the adsorbent with a flushing or rinsing gas, usually without an intentional effort to change the pressure or temperature of the system during the cycle), or combinations of any of these.

The hydrocarbon adsorption step can be carried out at high pressures, for example, at pressures up to about 20 bara (bar, absolute) or higher; however, it is usually carried out at pressures not in excess of about 5 bara. In general, it is preferred to conduct the hydrocarbon adsorption step at pressures that render this step most congruous with other steps of the overall process. The scrubbed gas from scrubber B is generally available at pressures up to about 2 bara. Operating the hydrocarbon adsorption process at adsorption pressures in the range of about 1.2 to about 1.75 bara will enable the scrubbed gas stream to pass through the hydrocarbon adsorbers and to reach a downstream incinerator (or other disposal means) without the use of supplemental blowers or compressors. Accordingly, it is preferred to conduct the adsorption step at pressures in the range of about 1.2 to about 1.75 bara.

The temperature at which the hydrocarbon adsorption is carried out is not critical. In general, the adsorption is carried out at temperatures in the range of about 5° C. to about 80° C., and it is most often carried out at temperatures in the range of about 20 to about 60° C. The adsorption is preferably carried out at the temperature which provides optimum separation and which is in harmony with other steps of the product manufacturing process, if possible. The optimum adsorption temperature of the process will depend, inter alia, upon the particular adsorbent being used, the temperature and relative humidity of the gas being separated, the pressure at which the process is carried out, the specific gases being separated, etc. Those skilled in the art can determine which operating conditions are best suited for their purposes.

A key feature of the hydrocarbon adsorption process is the step of purging the adsorption beds with air or oxygen-enriched air. This step serves the dual purpose of purging hydrocarbon from the beds and providing some or all of the oxygen required for the partial oxidation reaction. In CSA processes, and, to a considerable extent, in PSA-processes, the air purge step serves as the principal bed regeneration means. In PSA processes, the bed purge step may occur during the countercurrent depressurization step, or subsequent thereto as a separate step, or both during and after the countercurrent depressurization.

During part or all of the hydrocarbon adsorbent regeneration step(s), oxygen-containing gas is passed as a purge gas through the vessel(s) that are undergoing bed regeneration. It is often desirable to conduct the bed regeneration step at or near the temperature at which the adsorption step is carried out. The oxygen-containing gas used as a purge stream is generally introduced into the system at ambient temperature or hotter. The purge gas is ideally introduced into separator C at a pressure that will be sufficient to drive the purge gas through the hydrocarbon adsorption vessel being regenerated, and the offgas is sent back to reactor A through line 6, optionally with the aid of a feed air compressor (not shown). The desired pressure is often the minimum pressure necessary to cause the oxygen-containing gas to flow through the system. In general, the absolute pressure during the regeneration step of PSA cycles is usually in the range of about 20 millibara to about 2 bara. Although bed regeneration can be carried out at subatmospheric pressures, it is often preferable to avoid vacuum pressures, and to conduct this step at about atmospheric pressure or above, to avoid the use of high energy-consuming vacuum generating equipment. In preferred embodiments of the invention, regeneration of the hydrocarbon adsorbers is carried out at pressures in the range of about 1 to about 1.5 bara.

When the system illustrated in the drawing is employed in the process, the beds in vessels 42 and 44 are operated out of phase, with one bed in adsorption service while the other bed undergoes regeneration. A partial cycle (half-cycle) occurs when one bed has undergone all of the steps in the adsorption process. A full cycle occurs when each bed of the adsorption system has undergone a partial adsorption cycle. In the complete adsorption process full cycles are repeatedly carried out, so that the process is substantially continuous.

The operation of the separator C will be described first with the bed in vessel 42 in the adsorption mode and the bed in vessel 44 in the regeneration mode, and then the bed in vessel 44 in the adsorption mode and the bed in vessel 42 in the regeneration mode. In describing this embodiment, it is assumed that the gas stream enters separator C at superatmospheric pressure and bed regeneration takes place at or slightly above atmospheric pressure. In the first half of the cycle, valves 46, 58, 74 and 80 are open and all other valves associated with separator C are closed. The scrubbed moisture-containing feed gas passes through valve 46 and line 48 and enters vessel 42. As the gas passes through the adsorbent in this bed, unreacted hydrocarbon is preferentially adsorbed therefrom. The moisture-containing gas stream leaving vessel 42, now depleted in hydrocarbon, passes through line 56 and valve 58 and leaves the adsorption system through manifold 54 and line 64.

During part or all of the bed regeneration step(s), oxygen-containing gas, preferably air having a relative humidity less than 100%, is introduced into the vessel 44 through line 66, manifold 70, valve 74 and line 60. If the bed purge step is to be conducted at superatmospheric pressure, the oxygen-containing gas is pressurized to the desired pressure by means of optional blower 68. If the purge step is to be conducted at lower pressures, blower 68 can be eliminated, and the desorbed hydrocarbon and purge gas can be drawn back to reactor A by means of a feed gas compressor in line 6 (not shown). The purge gas may be at ambient temperature or hotter. In the latter case, the purge gas can be heated by compressing it, or by means of an optional heater (not shown). During the purge step, air or oxygen-enriched air passes through the adsorption bed in vessel 44, thereby desorbing hydrocarbon from the bed and sweeping the desorbed hydrocarbon from the vessel. The desorbed hydrocarbon and purge gas leave vessel 44 through line 52 and valve 80, and are conveyed to reactor A through line 6.

As the adsorption step proceeds, the unreacted hydrocarbon adsorbed gas front progresses through the bed in vessel 42 toward the outlet end of this vessel. When the adsorbed hydrocarbon front reaches a predetermined point in vessel 42, the first half of the cycle is terminated and the second half is begun.

During the second half of the adsorption cycle, the bed in vessel 44 is put into adsorption service and the bed in vessel 42 is regenerated. During this half-cycle valves 50, 62, 72 and 78 are open and all other valves associated with separator C are closed. Unreacted hydrocarbon gas now enters vessel 44 through line 52, passes through the bed of adsorbent in this vessel, and exits separator C through line 60, valve 62, manifold 54 and line 64. Meanwhile the bed in vessel 42 is being regenerated. During regeneration of the bed in vessel 42, the purge gas passes into vessel 42 via line 66, manifold 70, valve 72 and line 56, and desorbed hydrocarbon and purge gas exit this vessel through line 48, valve 78 and manifold 76, and are conveyed to reactor A through line 6. When the hydrocarbon adsorption front reaches a predetermined point in the bed in vessel 44, the second half of the cycle is terminated and the full cycle is repeated.

It will be appreciated that it is within the scope of the present invention to utilize conventional equipment to monitor and automatically regulate the flow of gases within the system so that it can be fully automated to run continuously in an efficient manner.

The invention is further illustrated by the following examples in which percentages, ratios, and parts, including parts per million (ppm), are on a volume basis, unless otherwise indicated.

The experiments described in the examples were carried out in a pair of 2.5 liter laboratory adsorption vessels that was 3" in diameter and 22" high with inert packing at each end. The feed gas, nonadsorbed gas (waste gas) and desorbed gas (product gas) streams were monitored and analyzed for composition using a Shimadzu gas chromatograph with a Thermal Conductivity Detector. The recoveries of butane and carbon dioxide were calculated based on the indicated measurements of the streams.

EXAMPLE I

In this example, a pair of laboratory adsorption vessels 1⅝" in diameter and 22" long and having inert packing at each end were used as the test vessels. The vessels were continuously operated alternately and out of phase on a CSA adsorption/purge cycle with a 4 minute full cycle time at a bed pressure near atmospheric and at ambient temperature. Each vessel was packed with about 590 grams of UOP silicalite adsorbent sold in pelletized form under the trade designation HISIV 3000. The average composition of the feed gas over the life of the experiment was: 1.8% n-butane, 7% carbon dioxide, and the balance nitrogen. Air was used as the purge gas. Both the feed gas and the purge air were saturated with moisture by bubbling these gases through water at room temperature. Analysis of each gas stream (feed gas, waste gas and product gas) was made on the first, fourth, eighth and eleventh days of the run. The results of the experiment are reported in the Table.

EXAMPLE II (COMPARATIVE)

The procedure of Example I was repeated except that the adsorption vessels were 3" in diameter and 22" long and had inert packing at each end and the adsorbent was 3×9 mesh silica gel sold by Davison Company under the trade designation Grade 41. Analysis of each gas stream (feed gas, waste gas and product gas) was made on the first, fourth, sixth, eighth and eleventh days of the run. The results of the experiment are reported in the Table.

TABLE

| | Example I | | Example II | |
|---|---|---|---|---|
| Day | n-Butane Recovery, % | Carbon dioxide Recovery, % | n-Butane Recovery, % | Carbon dioxide Recovery, % |
| First | 83 | 34 | 88 | 60 |
| Fourth | 86 | 32 | 87 | 45 |
| Sixth | — | — | 85 | 41 |
| Eighth | 86 | 32 | 83 | 35 |
| Eleventh | 86 | 33 | 45 | 15 |

The above examples illustrate the benefit of the invention. As shown in the Table, when a hydrophobic adsorbent (silicalite) was used to separate n-butane from the gas stream (Example I) the n-butane recovery and the carbon dioxide recovery remained substantially constant over the duration of the run. In contrast to this, when a conventional adsorbent (silica gel) was used for the separation (Example II), the n-butane recovery fell off significantly after the eighth day, and the carbon dioxide recovery fell off significantly after the first day and continually worsened as the run proceeded. The results indicate that moisture does not interfere with the adsorption of n-butane and carbon dioxide from a gas stream when moisture-saturated feed gas and moisture-saturated air purge gas are used in a CSA adsorption process using a hydrophobic adsorbent, but significantly interferes with the adsorption of n-butane and carbon dioxide from a gas stream when moisture-saturated feed gas and moisture-saturated air purge gas are used in a CSA adsorption process using a nonhydrophobic adsorbent.

Although the invention has been described with particular reference to a specific equipment configuration and to specific steps these are merely exemplary of the invention, and variations are contemplated. For example, the partial oxidation reaction can be carried out in the liquid phase or in mixed phases or under other conditions that will effect the production of other petrochemical products. Similarly, other catalysts can be used in the invention, if desired. Also, partial desaturation of the scrubbed gas from the product recovery unit can be accomplished by other techniques. For example, the gases can be partly dried by condensation or by use of a desiccant or a semipermeable membrane. The scope of the invention is limited only by the breadth of the appended claims.

What is claimed is:

1. A method of producing a petrochemical comprising the steps:

(a) contacting in a reaction zone a hydrocarbon with an oxygen-containing gas selected from the group consisting of air and oxygen-enriched air in the presence of an appropriate oxidation catalyst under conditions which produce a product gas containing said petrochemical, unreacted hydrocarbon and moisture;

(b) removing said petrochemical from said product gas in a petrochemical recovery zone, thereby producing a petrochemical-free unreacted hydrocarbon- and moisture-containing gas stream;

(c) passing at least part of said petrochemical-free unreacted hydrocarbon- and moisture-containing gas stream through a hydrophobic adsorbent, thereby adsorbing unreacted hydrocarbon onto said adsorbent;

(d) at least partially regenerating said adsorbent by passing an oxygen-containing gas selected from the group consisting of oxygen and oxygen-enriched air therethrough, thereby producing a gaseous stream comprising desorbed hydrocarbon and said oxygen-containing gas; and (e) recycling at least part of said gaseous stream to said reaction zone, thereby providing at least part of the oxygen-containing gas used in step (a).

2. The method of claim 1, wherein said hydrophobic adsorbent is a metal cation-free molecular sieve having a silicon-to-aluminum atomic ratio greater than about 100:1 selected from the group consisting of type Y zeolite, type ZSM-5 zeolite, type ZSM-11 zeolite, type ZSM-20 zeolite, silicalite-1, silicalite-2, and mixtures of these.

3. The method of claim 1 or claim 2, wherein steps (c) and (d) are steps of a cyclic adsorption process selected from the group consisting of CSA, PSA and combinations of these.

4. The improved method of claim 3, wherein steps (c) and (d) are each carried out at the same or different pressures in the range of about 1.2 to about 5 bara.

5. The improved method of claim 4, wherein steps (c) and (d) are carried out at substantially the same pressure.

6. The improved method of claim 5, wherein said pressure is in the range of about 1.2 to about 1.75 bara.

7. The improved method of claim 4, wherein steps (c) and (d) are carried out at different pressures.

8. The improved method of claim 7, further comprising between steps (c) and (d) the additional steps of desorbing hydrocarbon from said hydrocarbon-selective adsorbent by depressurization and recycling said desorbed hydrocarbon to said reaction zone.

9. The improved method of claim 3, wherein step (c) is carried out at a pressure in the range of about 1.2 to about 1.75 and step (d) is carried out at a pressure in the range of about 1 to about 1.5 bara.

10. The method of claim 1 or claim 2, further comprising reducing the relative humidity of one or both of said petrochemical-free gas stream and said oxygen-containing gas prior to passing them through said bed of adsorbent.

11. The method of claim 10, wherein the relative humidity of said petrochemical-free gas stream is reduced by heating this stream.

12. The method of claim 11, further comprising passing said petrochemical-free gas stream through a water cooler prior to heating this stream.

13. The method of claim 11, wherein said petrochemical-free gas stream is heated by compression.

14. The method of claim 10, wherein the relative humidity of said oxygen-containing gas is reduced by heating it prior to step (d).

15. The method of claim 14, wherein said oxygen-containing gas is heated by compression.

16. The method of claim 1 or claim 2, wherein during step (c) the temperature of said adsorbent is higher than the temperature of said petrochemical-free gas.

17. The method of claim 2, wherein said adsorbent is selected from the group consisting of type Y zeolite, type ZSM-5 zeolite, silicalite-1 and mixtures of these.

18. The method of claim 1, wherein said oxygen-containing gas is air.

19. The method of claim 18, wherein said air is ambient air.

20. The method of claim 19, wherein said adsorbent is silicalite.

21. The method of claim 1 or claim 2, wherein said petrochemical is maleic anhydride and said hydrocarbon is n-butane.

22. The method of claim 1 or claim 2, wherein part of said petrochemical-free gas stream is recycled directly to said reaction zone.

23. The method of claim 1 or claim 2, wherein said petrochemical is acrylonitrile and said hydrocarbon is propane or propylene.

24. The method of claim 1, further comprising introducing supplemental oxygen-containing gas into said reaction zone.

25. Apparatus for the production of petrochemicals comprising:
   (a) a partial oxidation reactor having a hydrocarbon inlet, an oxygen-containing gas inlet and a petrochemical product stream outlet;
   (b) a petrochemical recovery unit having a feed inlet, a petrochemical product outlet and a petrochemical-depleted gas outlet;
   (c) an adsorption system comprising at least one adsorption vessel, each of said at least one adsorption vessel containing a hydrophobic adsorbent and having a feed inlet end and a nonadsorbed gas outlet;
   (d) means for providing fluid communication between the petrochemical product outlet of said partial oxidation reactor and the feed inlet of said petrochemical recovery unit;
   (e) means for providing fluid communication between the petrochemical-depleted gas outlet of said petrochemical recovery unit and the feed inlet end of said at least one adsorption vessel;
   (f) means for providing fluid communication between the feed inlet end of said at least one adsorption vessel and the oxygen-containing gas inlet of said partial oxidation reactor;
   (g) means for providing a stream of oxygen-containing gas selected from the group consisting of air and oxygen-enriched air to the outlet end of said at least one adsorption vessel; and
   (h) means for directing said stream of oxygen-containing gas through said at least one adsorption vessel and then through said means for providing fluid communication between the feed inlet end of said at least one adsorption vessel and the oxygen-containing gas inlet of said partial oxidation reactor.

26. The apparatus of claim 25, further comprising means for pressurizing said stream of oxygen-containing gas.

27. The apparatus of claim 26, further comprising means for drying said stream of oxygen-containing gas.

28. The apparatus of claim 25, further comprising means for removing moisture from gas passing through said means for providing fluid communication between the petrochemical-depleted gas outlet of said petrochemical recovery unit and the feed inlet end of said at least one adsorption vessel.

29. The apparatus of claim 25, further comprising means for providing fluid communication between the petrochemical-depleted gas outlet of said petrochemical recovery unit and the oxygen-containing gas inlet of said partial oxidation reactor.

30. The apparatus of claim 25, wherein said hydrophobic adsorbent is a metal cation-free molecular sieve having a silicon-to-aluminum atomic ratio greater than about 100:1 selected from the group consisting of type Y zeolite, type ZSM-5 zeolite, type ZSM-11 zeolite, type ZSM-20 zeolite, silicalite-1, silicalite-2, and mixtures of these.

31. The apparatus of claim 25, wherein said adsorption system is a cyclic adsorption system selected from the group consisting of pressure swing adsorption systems, concentration swing adsorption systems and mixtures of these.

32. The apparatus of claim 31, wherein said hydrophobic adsorbent is selected from the group consisting of type Y zeolite, type ZSM-5 zeolite, silicalite-1 and mixtures of these.

* * * * *